US012672839B2

(12) United States Patent
Shan

(10) Patent No.: US 12,672,839 B2
(45) Date of Patent: Jul. 7, 2026

(54) RUBBER TUBE FOR STETHOSCOPE AND STRUCTURE FOR FITTING THE RUBBER TUBE WITH EAR-HUNG PIECES

(71) Applicant: WUXI KAISHUN MEDICAL DEVICE MANUFACTURING CO., LTD., Wuxi (CN)

(72) Inventor: Xijie Shan, Wuxi (CN)

(73) Assignee: WUXI KAISHUN MEDICAL DEVICE MANUFACTURING CO., LTD., Wuxi (CN)

( * ) Notice: Subject to any disclaimer, the term of this patent is extended or adjusted under 35 U.S.C. 154(b) by 700 days.

(21) Appl. No.: 18/558,739

(22) PCT Filed: Aug. 6, 2021

(86) PCT No.: PCT/CN2021/111153
§ 371 (c)(1),
(2) Date: Nov. 2, 2023

(87) PCT Pub. No.: WO2022/028569
PCT Pub. Date: Feb. 10, 2022

(65) Prior Publication Data
US 2024/0293098 A1 Sep. 5, 2024

(30) Foreign Application Priority Data

Aug. 7, 2020 (CN) .......................... 202021628383.4
Oct. 9, 2020 (CN) .......................... 202022230382.0

(51) Int. Cl.
*A61B 7/02* (2006.01)
(52) U.S. Cl.
CPC .................................... *A61B 7/02* (2013.01)

(58) Field of Classification Search
CPC ........................................................ A61B 7/02
(Continued)

(56) References Cited

U.S. PATENT DOCUMENTS 1,585,407 A * 5/1926 Morin ...................... A61B 7/02
181/135
3,108,652 A * 10/1963 Littmann ............... A61B 7/026
D24/134
(Continued)

FOREIGN PATENT DOCUMENTS

CN 2662833 Y 12/2004
CN 202801657 U 3/2013
(Continued)

OTHER PUBLICATIONS

International Search Report w/English translation for PCT /CN2021/ 111153 mailed Nov. 10, 2021, 6 pages.
(Continued)

*Primary Examiner* — Jeremy A Luks
(74) *Attorney, Agent, or Firm* — Nixon & Vanderhye P.C.

(57) ABSTRACT

A rubber tube for a stethoscope and a structure for fitting the rubber tube with ear-hung pieces. The rubber tube (1) for a stethoscope comprises a rubber tube channel (10) penetrating through each end portion, recesses (12) are provided on a channel wall (11) of the rubber tube channel (10); and when the ear-hung pieces are opened towards two sides for use, the sound listening effect of the stethoscope will not be reduced due to an ear-hung piece spring plate (71) pressing the channel wall (11) of the rubber tube (1).

9 Claims, 10 Drawing Sheets

(58) Field of Classification Search
USPC ......................................................... 181/131
See application file for complete search history.

(56) References Cited

U.S. PATENT DOCUMENTS

| | | | | | |
|---|---|---|---|---|---|
| 3,152,659 | A | * | 10/1964 | Littmann | A61B 7/026 |
| | | | | | D24/134 |
| 3,168,160 | A | * | 2/1965 | Littmann | A61B 7/02 |
| | | | | | 181/135 |
| 3,346,069 | A | * | 10/1967 | Speelman | A61B 7/02 |
| | | | | | D24/134 |
| 3,437,172 | A | * | 4/1969 | Allen | A61B 7/026 |
| | | | | | 181/131 |
| 3,504,760 | A | * | 4/1970 | Littmann | A61B 7/026 |
| | | | | | 181/135 |
| 3,618,697 | A | * | 11/1971 | Littmann | A61B 7/02 |
| | | | | | 181/135 |
| 3,735,836 | A | * | 5/1973 | Littmann | A61B 7/02 |
| | | | | | 181/131 |
| 4,029,169 | A | * | 6/1977 | Huntress | A61B 7/02 |
| | | | | | 181/135 |
| 4,200,169 | A | * | 4/1980 | MacDonald, III | A61B 7/026 |
| | | | | | 181/135 |
| 4,569,413 | A | * | 2/1986 | Allen | A61B 7/026 |
| | | | | | 181/131 |
| 5,111,904 | A | * | 5/1992 | Packard | A61B 7/02 |
| | | | | | 181/175 |
| 5,288,954 | A | * | 2/1994 | Peart | A61B 7/02 |
| | | | | | 181/131 |
| 5,883,340 | A | * | 3/1999 | Shieh | A61B 7/02 |
| | | | | | 181/131 |
| 6,454,045 | B1 | * | 9/2002 | Ryan | A61B 7/02 |
| | | | | | 600/528 |
| 12,011,313 | B2 | * | 6/2024 | Ting | G10K 11/08 |

FOREIGN PATENT DOCUMENTS

| | | |
|---|---|---|
| CN | 104644161 A | 5/2015 |
| CN | 105433976 A | 3/2016 |
| CN | 210494101 U | 5/2020 |
| DE | 1226242 B | 10/1966 |
| JP | 4968940 B2 | 4/2012 |

OTHER PUBLICATIONS

Written Opinion of the ISA w/English translation for PCT /CN2021/ 111153 mailed Nov. 10, 2021, 11 pages.
International Preliminary Report on Patentability w/English translation for PCT /CN2021/111153 dated Feb. 7, 2023, 12 pages.

* cited by examiner

RUBBER TUBE FOR STETHOSCOPE AND STRUCTURE FOR FITTING THE RUBBER TUBE WITH EAR-HUNG PIECES

CROSS-REFERENCE TO RELATED APPLICATIONS

This application is the U.S. national phase of International Application No. PCT/CN2021/111153 filed Aug. 6, 2021, which designated the U.S. and claims priority to CN 202022230382.0 filed Oct. 9, 2020, and CN 202021628383.4 filed Aug. 7, 2020, the entire contents of each of which are hereby incorporated by reference.

TECHNICAL FIELD

The present disclosure relates to a rubber tube for a stethoscope and a combined structure of the rubber tube and ear hooks, in particular, in which sound loudness of the stethoscope may not be reduced due to pressure against a channel wall of the rubber tube by an elastic sheet of the ear hooks when the ear hooks are forced away from each other in use.

BACKGROUND TECHNOLOGY

The stethoscopes in the prior art are defective as below.

As shown in FIGS. 1 and 2, left and right ends of an elastic sheet 71 are respectively connected to a left ear tube 51 and a right ear tube 61. An end 52 of the left ear tube towards the elastic sheet, an end 62 of the right ear tube towards the elastic sheet and the elastic sheet 71 are disposed within a channel 10 of a rubber tube 1 and tightly fitted with a channel wall 11 of the channel. When the left ear tube 51 and the right ear tube 61 are forced away from each other in use of the stethoscope, the elastic sheet 71 presses against the channel wall 11 of a lower part of the channel 10 of the rubber tube 1, such that the communication between channel 10 and a channel 53 of the left ear tube as well as the communication between the channel 10 and a channel 63 of the right ear tube are blocked, thereby reducing a loudness of the sound transmitted from organs via the stethoscope and affecting an auscultation effect of the stethoscope.

In the existing design, the rubber tube 1 has only one channel defined by an inner wall of the channel of the rubber tube. Once the elastic sheet 71 presses against the channel wall 11 of the lower part of the channel 10 of the rubber tube 1, the channel 10 is blocked, so the auscultation effect of the stethoscope is degraded.

Therefore, a technical problem to be solved urgently in the industry is to provide a rubber tube for a stethoscope and a combined structure of the rubber tube and ear hooks, which can ensure that a sound guiding channel of the stethoscope is not blocked and the auscultation effect of the stethoscope may not be affected when the left and right ear tubes are forced away from each other such that the elastic sheet presses against the wall of the channel of the rubber tube.

SUMMARY OF THE INVENTION

One of objects of the present disclosure is to provide a rubber tube for a stethoscope.

One of the objects of the present disclosure is achieved by the following solution.

A rubber tube for a stethoscope is provided with a rubber tube channel running through each end portion of the rubber tuber, and a groove is formed in a channel wall of the rubber tube channel. The rubber tube includes ear-hook tubes and a stethoscope-head tube which are connected to each other, the rubber tube channel comprises channels of the ear-hook tubes and a channel of the stethoscope-head tube that communicates with the channels of the ear-hook tubes, and the groove is arranged in inner walls of the ear-hook tubes and communicates with the channel of the stethoscope-head tube. The ear-hook tubes may be formed integrally with the stethoscope-head tube. The groove may be provided in a number of 1, 2, 3 or above.

In the above solution, at least two channels, which are intersected and communicate with each other, are provided in each of the left and right ear-hook tubes, where the annular inner wall of the ear-hook tube constitutes the rubber tube channel, and a bottom side and side walls of the groove together define a groove channel.

In the above solution, a first convex rib may be provided on an inner bottom surface of a U-shaped portion of the rubber tube. After the left and right ear tubes are fitted with the rubber tube, the first convex rib facilitates the fitting of the left and right ear tubes with the ear canals of a user during the use of the stethoscope by the user, and when the user takes off the stethoscope, the first convex rib facilitates the restoring of the rubber tube to its original shape.

In the above solution, second convex ribs may be provided on an outer bottom surface of the U-shaped portion of the rubber tube at both sides of the U-shaped portion. After the left and right ear tubes are fitted with the rubber tube, the second convex ribs facilitate the fitting of the left and right ear tubes with the ear canals of a user during the use of the stethoscope the user, and when the user takes off the stethoscope, the second convex ribs facilitate the restoring of the rubber tube to its original shape.

Another one of the objects of the present disclosure is to provide a combined structure of a rubber tube and ear hooks.

The technical solution of the present disclosure is provided as below.

A combined structure of a rubber tube and ear hooks includes the above-described rubber tube and the ear hooks, where, the ear hooks include a left ear tube, a right ear tube and an elastic sheet connecting the left and right ear tubes: an end of the left ear tube towards the elastic sheet, an end of the right ear tube towards the elastic sheet and the elastic sheet are disposed within the channel of the rubber tube, so that the end of the left ear tube towards the elastic sheet and the end of the right ear tube tightly towards the elastic sheet fit with the inner walls of the ear-hook tubes; and when the left and right ear tubes are forced away from each other and thus a lower surface of the elastic sheet presses against the inner bottom walls of the ear-hook tubes, the channel of the stethoscope-head tube communicates with the channels of the ear-hook tubes through the groove so that at least part of the sound is transmitted to the channels of the left and right ear tubes through the groove.

Still another one of the objects of the present disclosure is to provide a combined structure of a rubber tube and ear hooks.

The technical solution of the present disclosure is provided as below.

A combined structure of a rubber tube and ear hooks includes the above-described rubber tube, ear hooks and a T-shaped connector. The ear hooks include a left ear tube, a right ear tube and an elastic sheet connecting the left and right ear tubes; an end of the left ear tube towards the elastic sheet, an end of the right ear tube towards the elastic sheet and the elastic sheet are disposed within the channel of the rubber tube, so that the end of the left ear tube towards the elastic sheet and the end of the right ear tube towards the elastic sheet tightly fit with the inner walls of the ear-hook tubes: the connector is provided with a three-way channel running through wings and a lower part of the connector; the wings of the connector are embedded in the groove, and the three-way channel communicates with the groove; the connector is located below the elastic sheet; and when the left and right ear tubes are forced away from each other and thus the lower surface of the elastic sheet presses against the top surface of the connector, the channel of the stethoscope-head tube communicates with the channels of the ear-hook tubes through the three-way channel of the connector and the groove.

In the above technical solution, the T-shaped connector in the combined structure contains a three-way channel running through its two wings and the lower part, the two wings of the connector are embedded in the groove, and the three-way channel communicates with the groove.

In the above technical solution, after the wings of the connector are embedded in the groove, the top surface of the connector is not higher than the inner bottom wall of the ear-hook tube.

In the above technical solution, a horizontal part of the connector has a width equal to or below that of the elastic sheet. That is, when the elastic sheet presses against the top surface of the connector, the elastic sheet cannot fall into the channels of the wings.

In the above technical solution, a first convex rib is provided on an inner bottom surface of a U-shaped portion of the rubber tube.

In the above technical solution, second convex ribs are provided on an outer bottom surface of the U-shaped portion of the rubber tube at both sides of the U-shaped portion.

In the above three technical solutions, with the design of the dual-channel ear-hook tube, the problem of degrading the auscultation of the existing stethoscope due to the blocking of the single channel of the ear-hook tube is effectively avoided. The rubber tube channel includes channels of the ear-hook tubes and a channel of the stethoscope-head tube, and the channel of the ear-hook tube includes a first channel and a second channel, where the first channel is enclosed by the inner wall of the ear-hook tube, and the second channel is the groove which is disposed in the inner wall of the ear-hook tube to be open towards the first channel from the inner wall of the ear-hook tube.

When the combined structure of the rubber tube and the ear hooks is provided with a connector, the second channel further includes a channel of a horizontal part (which includes wings on both lateral sides of the connector) of the connector.

The advantages of the present disclosure are described as below.

1. The groove in the rubber tube of the present disclosure effectively avoids the deterioration of the auscultation effect of the stethoscope due to the pressing of the elastic sheet against the wall of the rubber tube channel in the prior art.

2. The convex rib provided on the inner bottom surface of the U-shaped portion of the rubber tube of the present disclosure and the convex ribs provided on the outer bottom surface of the U-shaped portion can improve the fitness between the left and right ear tubes and the auricle.

3. With the dual-channel rubber tube for sound guiding of the disclosure, when the first channel in the dual channels is blocked, the second channel can always be kept unblocked, thereby effectively avoiding the deterioration of the auscultation effect of the stethoscope due to the pressing of the elastic sheet against the wall of the rubber tube channel.

| List of Reference Signs: | | |
| --- | --- | --- |
| 1: rubber tube | 10: channel | 10a: channel of ear-hook tube |
| 10b: channel of stethoscope-head tube | | 11: channel wall |
| 11a: inner bottom wall of ear-hook tube | | 12: groove |
| 20: U-shaped portion | 21: inner bottom surface | |
| 22: outer bottom surface | 23: first convex rib | 24: second convex rib |
| 51: left ear tube | 52: end of left ear tube towards elastic sheet | |
| 53: channel of left ear tube | | |
| 61: right ear tube | 62: end of right ear tube towards elastic sheet | |
| 63: channel of right ear tube | | |
| 71: elastic sheet | | |
| 8: connector | 8a: wing | 8b: lower part |
| 8c: horizontal part | 80: three-way channel | |
| 81: top surface of connector | | 80a: wing channel |
| 80b: lower channel | D2: width of horizontal part | |

SPECIFIC EMBODIMENTS OF THE INVENTION

The present disclosure will be further described below in conjunction with the drawings. The following embodiments are only preferred examples and are not intended to limit the scope of the present disclosure. On the contrary, the embodiments are aimed in that the various modifications, their equivalents and various combinations thereof of the embodiments described in the present disclosure are covered by the scope of the present invention.

Figure 1:
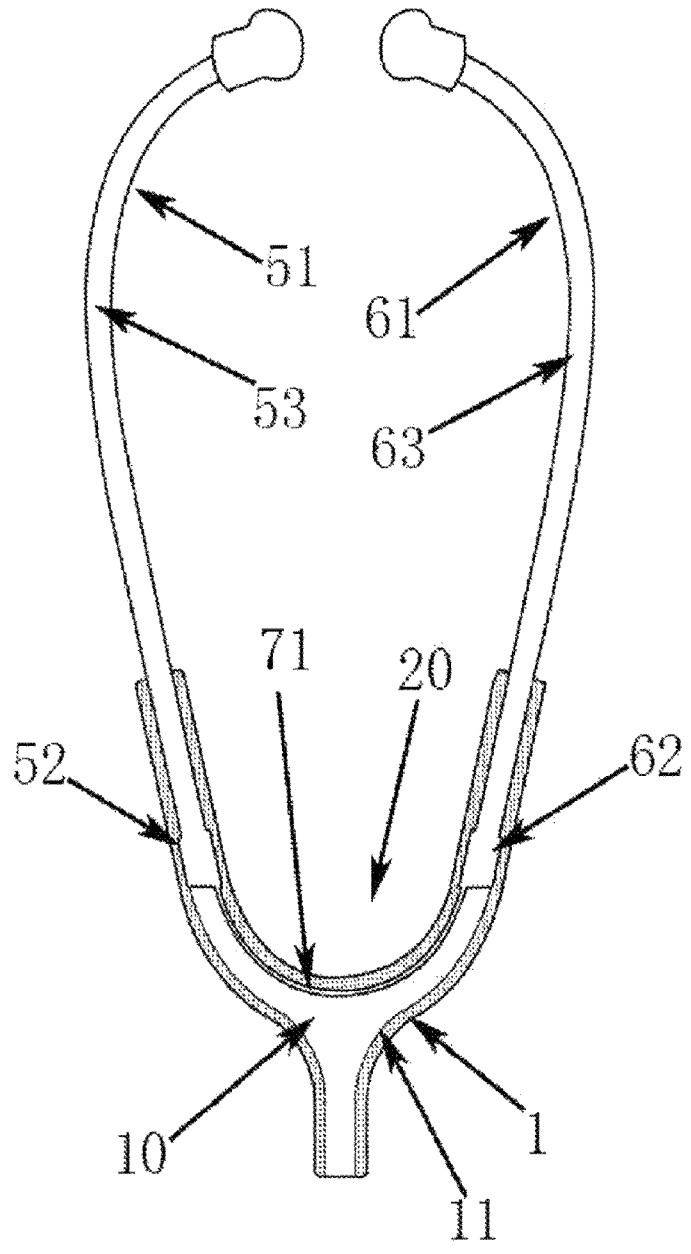
FIG. 1 is a first schematic diagram of a combined structure of a rubber tube and ear hooks for a stethoscope in the prior art.
Figure 2:
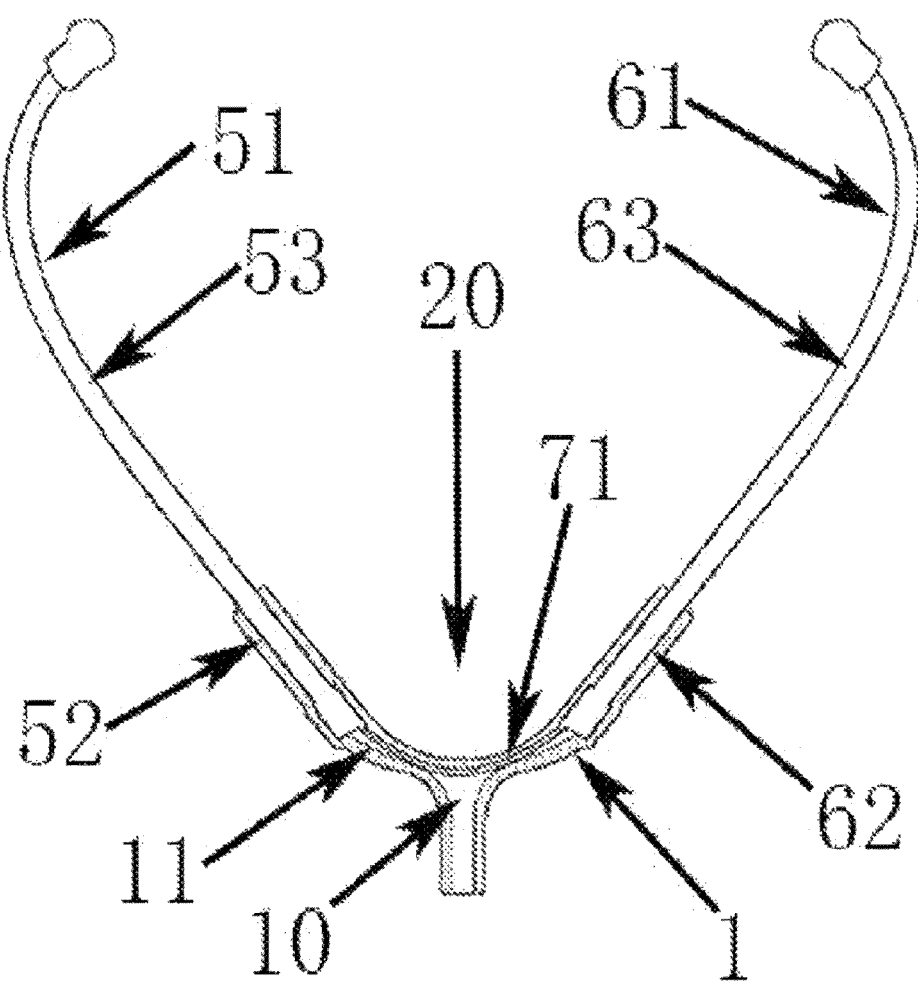
FIG. 2 is a second schematic diagram of the combined structure of the rubber tube and the ear hooks for the stethoscope in the prior art.
Figure 3:
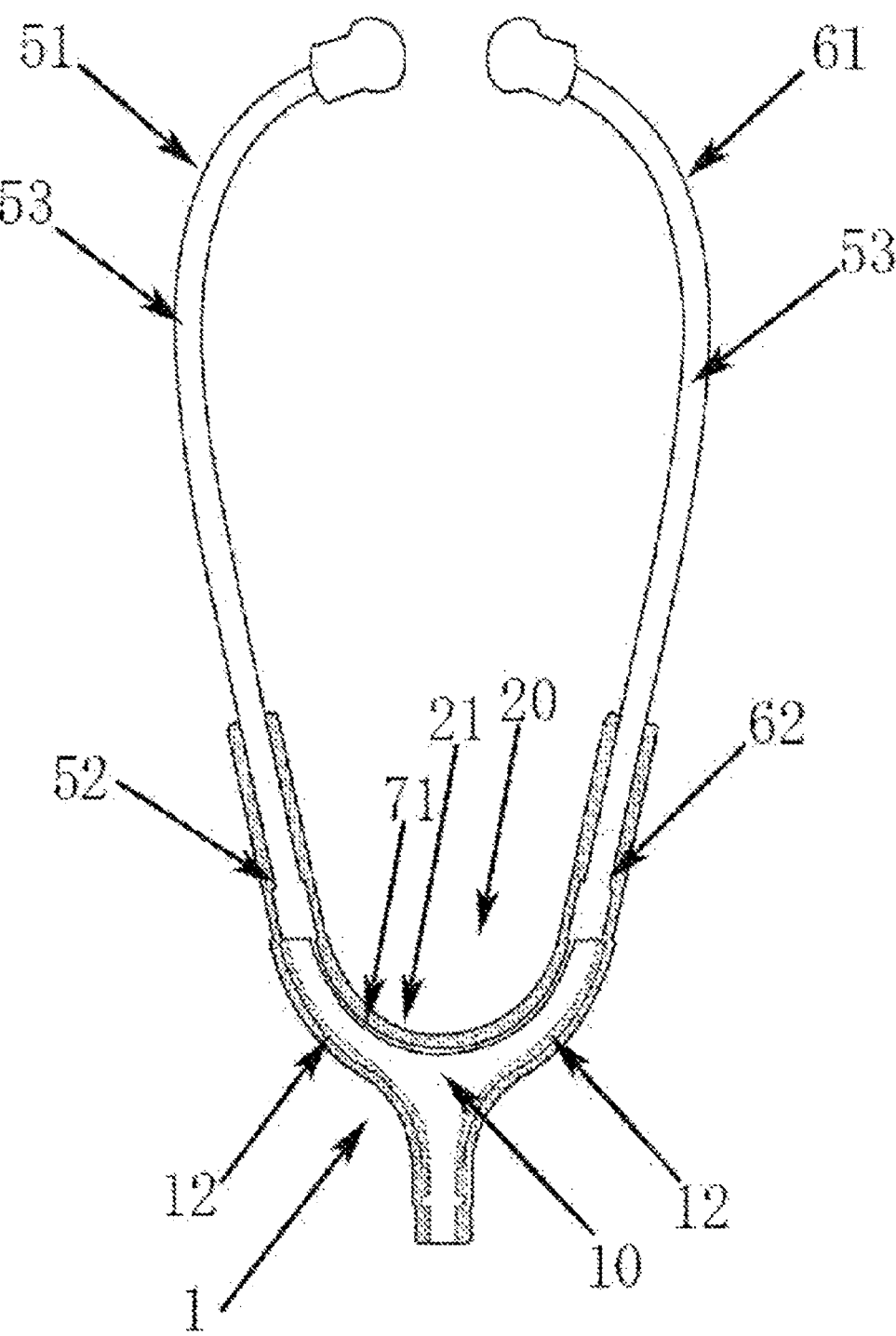
FIG. 3 is a first schematic diagram of a combined structure of a rubber tube and ear hooks for a stethoscope according to an embodiment of the present invention.
Figure 4:
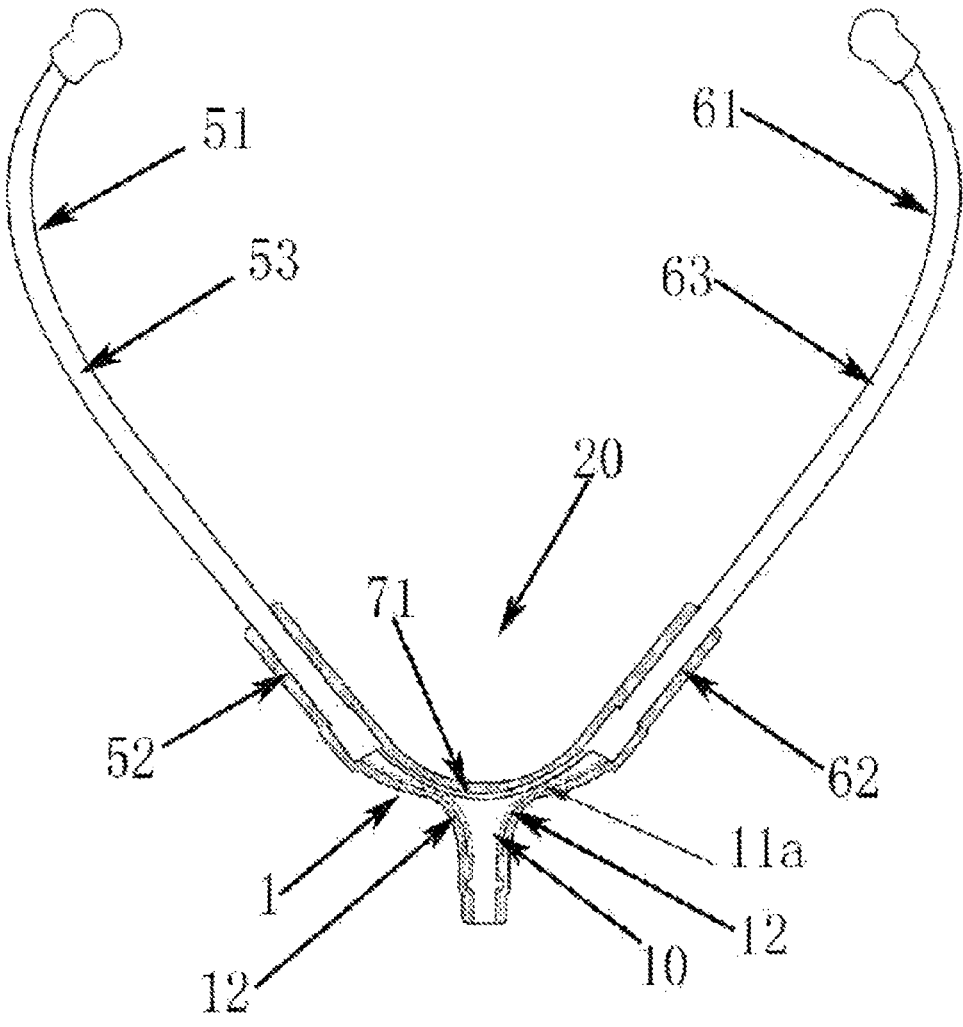
FIG. 4 is a second schematic diagram of the combined structure of the rubber tube and the ear hooks for the stethoscope according to the embodiment of the present invention.
Figure 5:
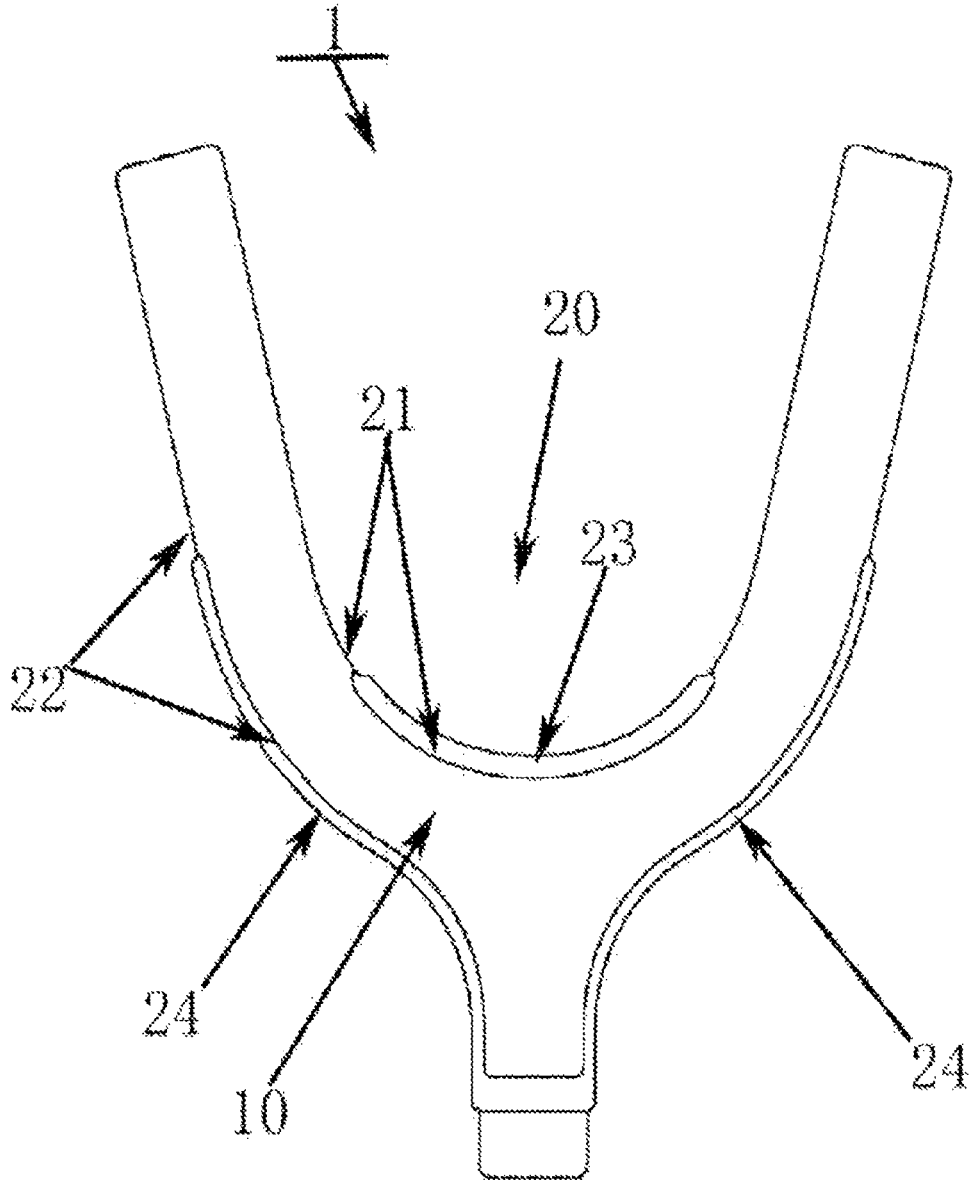
FIG. 5 is a schematic diagram of a rubber tube for a stethoscope according to another embodiment of the present invention.
Figure 6:
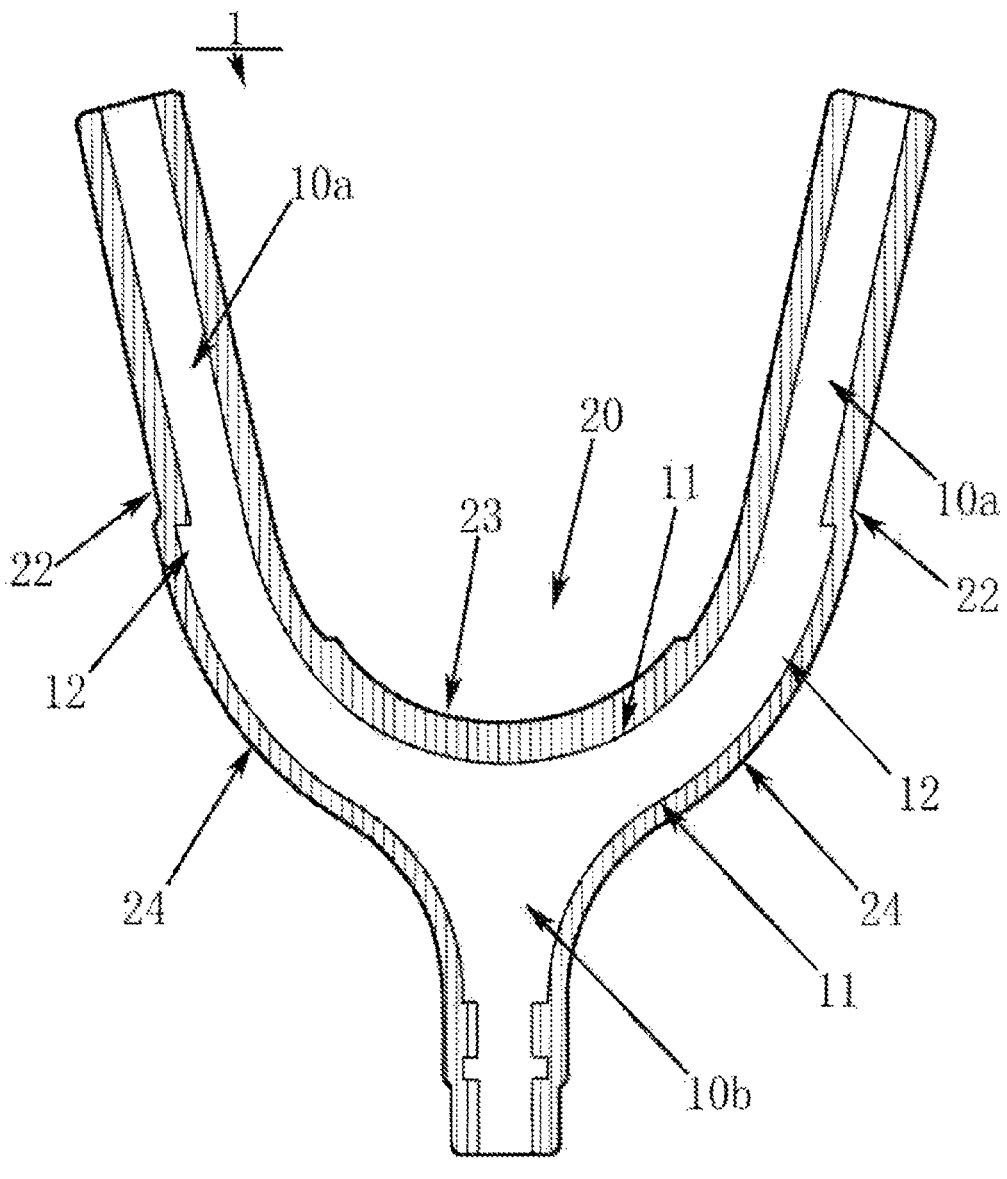
FIG. 6 is a schematic cross-sectional view of the rubber tube for the stethoscope of the present disclosure.
Figure 7:
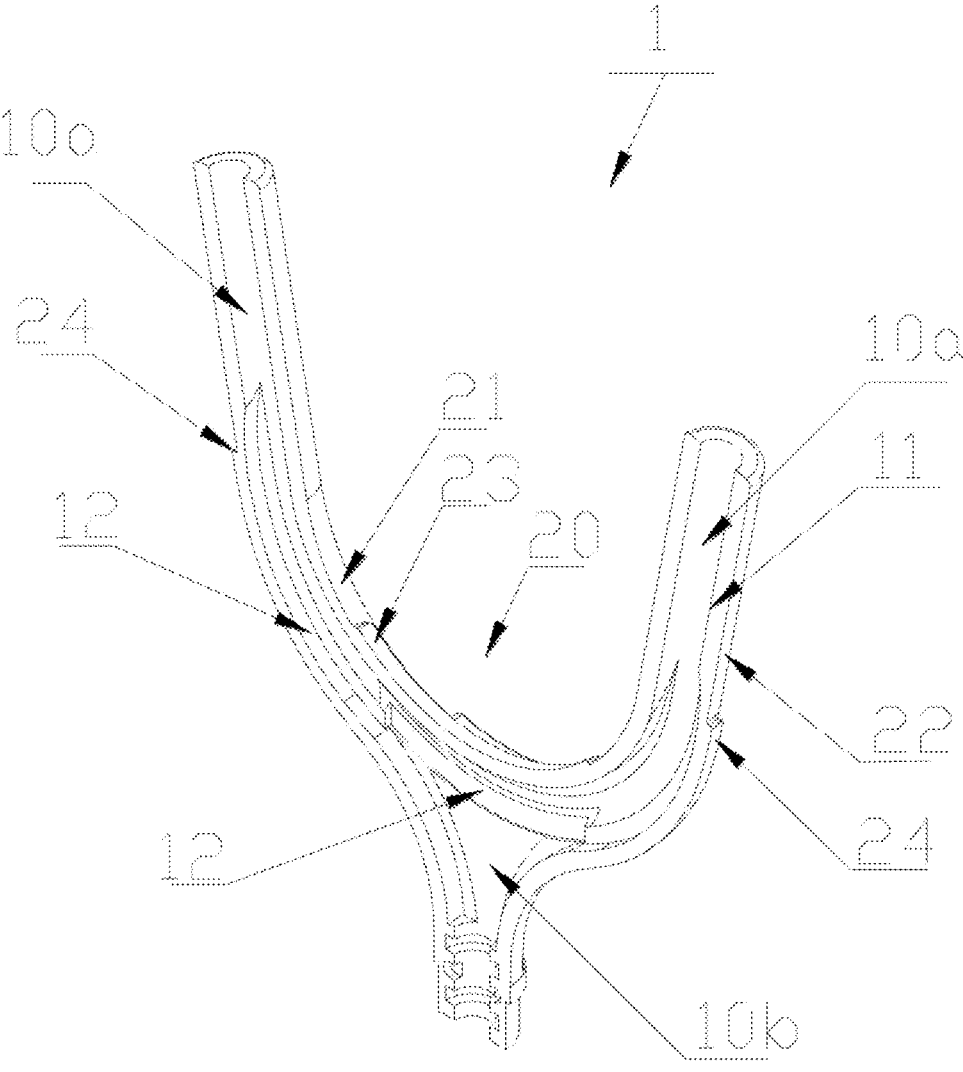
FIG. 7 is a perspective cross-sectional view of the rubber tube for the stethoscope of the present disclosure.
Figure 8:
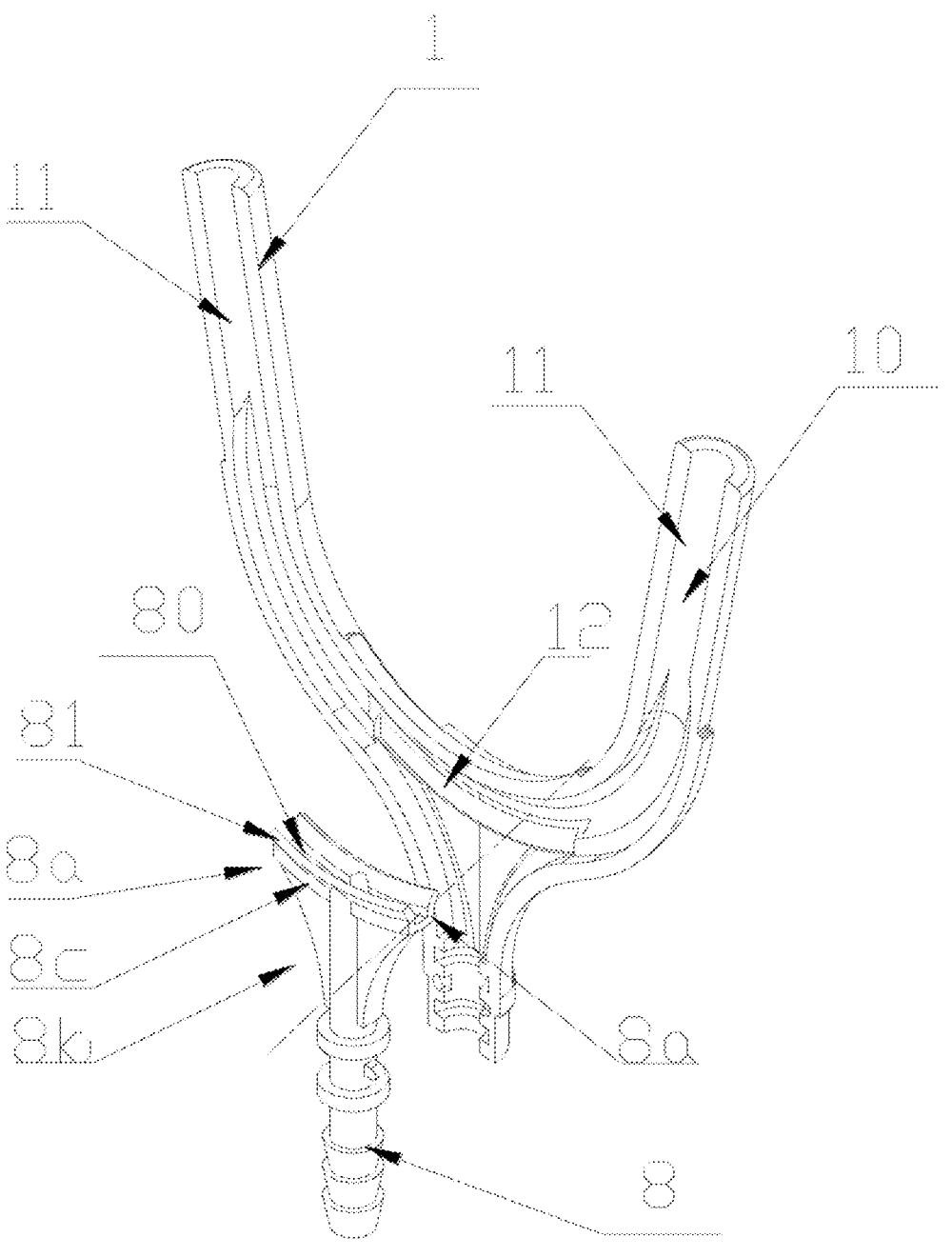
FIG. 8 is a schematic diagram of the combined structure of the rubber tube for the stethoscope and a connector according to the present disclosure.
Figure 9:
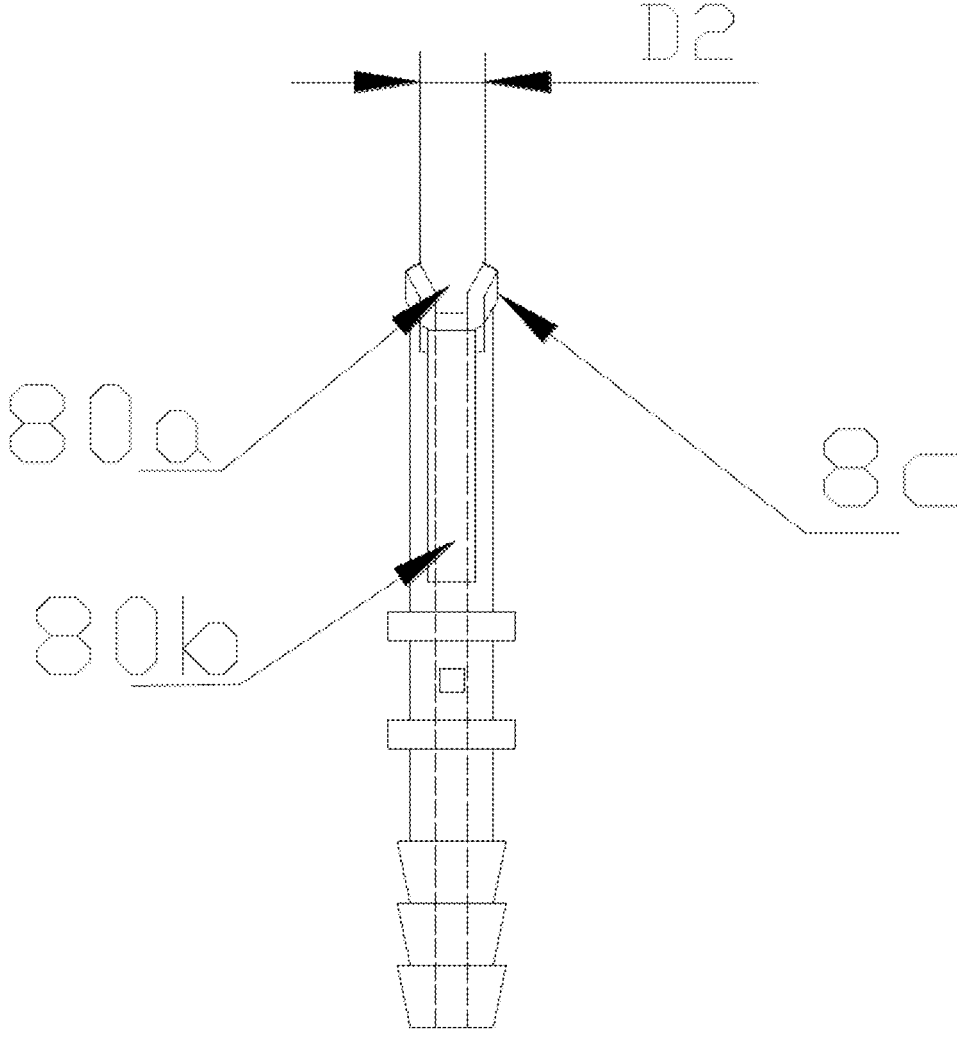
FIG. 9 is a schematic side view of the connector of the present disclosure.
Figure 10:
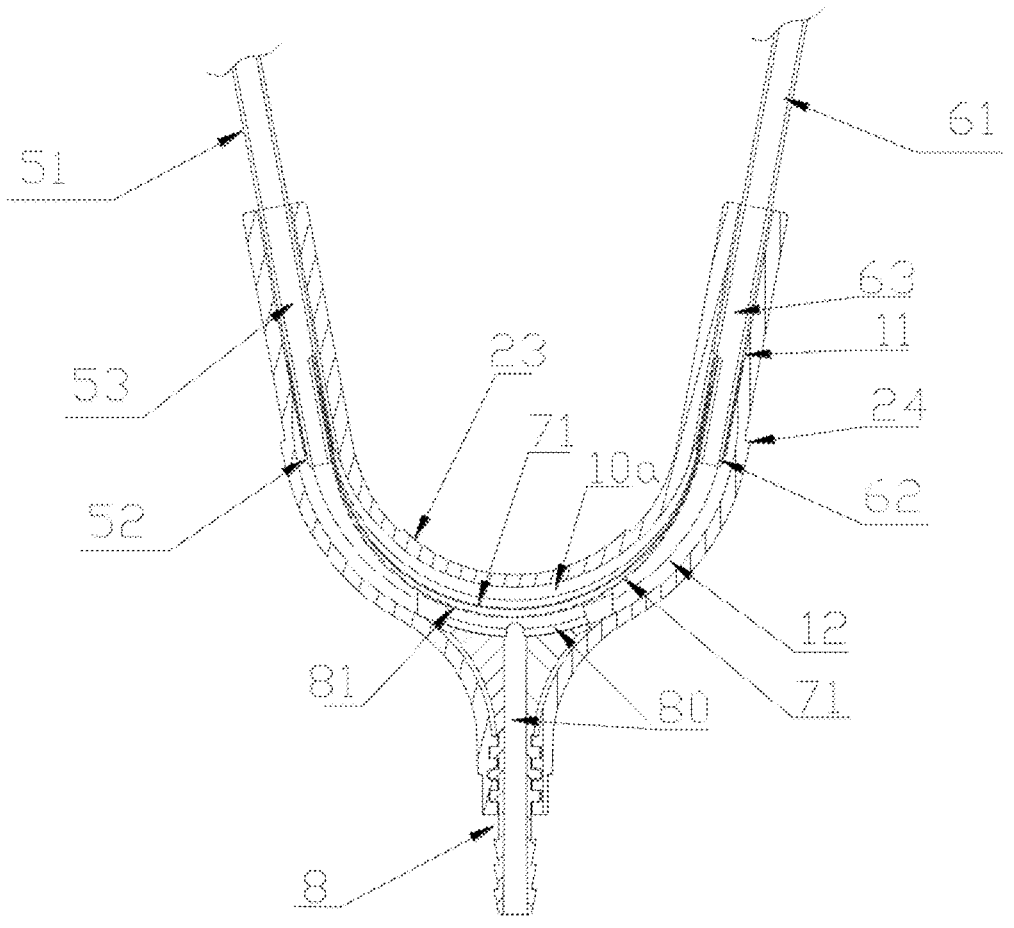
FIG. 10 is a schematic diagram of the combined structure of the rubber tube for the stethoscope, the ear hooks and the connector according to the present disclosure.

Embodiment 1: A first embodiment of the present invention will be described below in conjunction with FIGS. 5 and 6

The rubber tube 1 for a stethoscope provided in the first embodiment is provided with a channel 10 running through each end portion thereof, and a groove 12 is formed in the channel wall 11 of the channel 10.

The rubber tube 1 includes a U-shaped portion 20, two end portions of which are respectively used to connect with a left ear tube and a right ear tube of ear hooks and thus may also be called as ear-hook tubes. A portion extending from a bottom of the U-shaped portion 20 and communicating with the U-shaped portion 20 is used for connecting with a head of the stethoscope, and thus may also be called as a stethoscope-head tube.

A first convex rib 23 may be provided on an inner bottom surface 21 of the U-shaped portion 20. Herein, the inner side of the U-shaped portion 20 refers to a space together defined by the two end portions of the U-shaped portion 20 and the bottom connecting the two end portions, and the inner bottom surface 21 of the U-shaped portion 20 is located at the bottom of the inner side of the U-shaped portion 20.

In addition, second convex ribs 24 may be provided on an outer bottom surface 22 of the U-shaped portion 20 of the rubber tube 1 at both sides of the U-shaped portion 20.

In this embodiment, since the groove 12 is provided on the channel wall 11, even when an elastic sheet connecting the left and right ear tubes presses against the channel wall 11 of the rubber tube 1 in use and thus block the channel 10, the groove 12 will not be blocked by the elastic sheet due to its concave design, so that the stethoscope can always be kept unblocked during use and function to transmit the sound coming from the head of the stethoscope to the left and right ear tubes. In addition, the first convex rib 23 and the second convex rib 24 provided on the outer surface of the rubber tube 1 can improve the fitness between the eft and right ear tubes and auricles, so that even if the elasticity of the elastic sheet is reduced after a long use of the stethoscope, good fitness between the eft and right ear tubes and the auricles can be ensured.

Embodiment 2: A second embodiment is described below in conjunction with FIGS. 3 to 6

This embodiment provides a combined structure of a rubber tube and ear hooks, which includes a rubber tube 1 and ear hooks.

The rubber tube 1 is provided with a channel 10 running through each end portion thereof, and a groove 12 is formed in the channel wall 11 of the channel 10 and communicates with both a channel 10b of the stethoscope-head tube and channels 10a of the ear-hook tubes. A first convex rib 23 may be provided on the inner bottom surface 21 of the U-shaped portion 20 of the rubber tube 1, and second convex ribs 24 may be provided on the outer bottom surface 22 of the U-shaped portion 20 of the rubber tube 1 at both sides of the U-shaped portion 20.

The ear hooks include the left ear tube 51, the right ear tube 61 and the elastic sheet 71. Two ends of the elastic sheet 71 are respectively connected to the left ear tube 51 and the right ear tube 61.

The elastic sheet 71, an end 52 of the left ear tube towards the elastic sheet, and an end 62 of the right ear tube towards the elastic sheet are all disposed within the channel 10 of the rubber tube 1. The end 52 of the left ear tube towards the elastic sheet and the end 62 of the right ear tube towards the elastic sheet tightly fit with the channel wall 11 of the channel 10 of the rubber tube 1.

When the left ear tube 51 and the right ear tube 61 are forced away from each other so that the lower surface of the elastic sheet 71 presses against the inner bottom walls 11a of the ear-hook tubes, the channel 10b of the stethoscope-head tube communicates with the channels 10a of the ear-hook tubes through the groove 12, so that the sound can be communicated to a channel 53 of the left ear tube and a channel 63 of the right ear tube through the groove 12.

Embodiment 3: A third embodiment is described below in conjunction with FIGS. 7 to 10

This embodiment provides a combined structure of a rubber tube and ear hooks, which includes a rubber tube 1, ear hooks and a connector 8.

The rubber tube 1 is provided with a channel 10 running through each end portion thereof, and a groove 12 is formed in the channel wall 11 of the channel 10 and communicates with both a channel 10b of the stethoscope-head tube and channels 10a of the ear-hook tubes. A first convex rib 23 may be provided on the inner bottom surface 21 of the U-shaped portion 20 of the rubber tube 1, and second convex ribs 24 may be provided on the outer bottom surface 22 of the U-shaped portion 20 of the rubber tube 1 at both sides of the U-shaped portion 20.

The ear hooks include the left ear tube 51, the right ear tube 61 and the elastic sheet 71. Two ends of the elastic sheet 71 are respectively connected to the left ear tube 51 and the right ear tube 61.

The elastic sheet 71, an end 52 of the left ear tube towards the elastic sheet, and an end 62 of the right ear tube towards the elastic sheet are all disposed within the channel 10 of the rubber tube 1. The end 52 of the left ear tube towards the elastic sheet and the end 62 of the right ear tube towards the elastic sheet tightly fit with the channel wall 11 of the channel 10 of the rubber tube 1.

The connector 8 is T-shaped and is provided with two wings 8a and a lower part 8b. The connector 8 is provided with a three-way channel 80 running through the wings 8a and the lower part 8b. The three-way channel 80 includes a wing channel 80a and a lower channel 80b.

The two wings 8a of the connector 8 are embedded in the groove 12, so that the three-way channel 80 communicates with the groove 12. The connector 8 is located below the elastic sheet 7, and a width D2 of the horizontal part of the connector 8 is not larger, preferably smaller, than the width of the elastic sheet 7.

When the left ear tube 51 and the right ear tube 61 are forced away from each other so that the lower surface of the elastic sheet 71 presses against the top surface 81 of the connector 8, the channel 10b of the stethoscope-head tube communicates with the channels 10a of the ear-hook tubes through the three-way channel 80 of the connector 8 and the groove 12, and thus the sound can be transmitted to the channel 53 of the left ear tube and the channel 63 of the right ear tube through the groove 12.

To sum up, in the rubber tube of the present disclosure, in addition to the original rubber tube channel, another channel is also provided for communicating the channel 10b of the stethoscope-head tube and the channels 10a of the ear-hook tubes, so that in the case that the original rubber tube channel is blocked, the another channel can still be kept unblocked so as to maintain the communication between the channel 10b of the stethoscope-head tube and the channels 10a of the ear-hook tubes, without affecting the auscultation effect of the stethoscope. In addition, the convex rib on the inner bottom surface of the U-shaped portion and the convex ribs on the outer bottom surface of the U-shaped portion of the rubber tube of the present disclosure can improve the fitness between the left and right ear tubes and the auricles.

The present disclosure has been described above through the embodiments, which are intended to explain the present disclosure but not to limit the scope of the present disclosure. The above-described embodiments and features of the embodiments can be combined with each other without conflict.

The invention claimed is:

1. A combined structure of a rubber tube for a stethoscope and ear hooks, wherein the rubber tube comprises a rubber tube channel running through each end portion of the rubber tube, grooves are formed in a channel wall of the rubber tube channel, the rubber tube comprises ear-hook tubes and a stethoscope-head tube which are connected to each other, the rubber tube channel comprises channels of ear-hook tubes and a channel of the stethoscope-head tube that communicates with the channels of the ear-hook tubes, and the grooves are arranged in inner walls at the bottom of the ear-hook tubes and communicate with the channel of the stethoscope-head tube, the ear hooks comprise a left ear tube, a right ear tube and an elastic sheet connecting the left ear tube and the right ear tube; an end of the left ear tube towards the elastic sheet, an end of the right ear tube towards the elastic sheet and the elastic sheet are disposed within the channel of the rubber tube, so that the end of the left ear tube towards the elastic sheet and the end of the right ear tube towards the elastic sheet tightly fit with the inner walls of the ear-hook tubes; and when the left ear tube and the right ear tube are forced away from each other and thus a lower surface of the elastic sheet presses against the inner bottom walls of the ear-hook tubes, the channel of the stethoscope-head tube communicates with the channels of the ear-hook tubes through the grooves.

2. The combined structure of a rubber tube for a stethoscope and ear hooks according to claim 1, wherein at least two channels, which are intersected and communicate with each other, are provided in each of the ear-hook tubes, wherein an annular inner wall of the ear-hook tube constitutes the rubber tube channel, and a bottom side and side walls of the groove together define a groove channel.

3. The combined structure of a rubber tube for a stethoscope and ear hooks according to claim 1, wherein a first convex rib is provided on an inner bottom surface of a U-shaped portion of the rubber tube.

4. The combined structure of a rubber tube for a stethoscope and ear hooks according to claim 1, wherein second convex ribs are provided on an outer bottom surface of the U-shaped portion of the rubber tube at both sides of the U-shaped portion.

5. A combined structure of a rubber tube for a stethoscope and ear hooks, wherein the rubber tube comprises a rubber tube channel running through each end portion of the rubber tube, grooves are formed in a channel wall of the rubber tube channel, the rubber tube comprises ear-hook tubes and a stethoscope-head tube which are connected to each other, the rubber tube channel comprises channels of ear-hook tubes and a channel of the stethoscope-head tube that communicates with the channels of the ear-hook tubes, and the grooves are arranged in inner walls at the bottom of the ear-hook tubes and communicate with the channel of the stethoscope-head tube, the ear hooks comprise a left ear tube, a right ear tube and an elastic sheet connecting the left ear tube and the right ear tube; an end of the left ear tube towards the elastic sheet, an end of the right ear tube towards the elastic sheet and the elastic sheet are disposed within the channel of the rubber tube, so that the end of the left ear tube towards the elastic sheet and the end of the right ear tube towards the elastic sheet tightly fit with the inner walls of the ear-hook tubes; the structure further comprises a T-shaped connector which is provided with a three-way channel running through wings and a lower part of the T-shaped connector; the wings of the T-shaped connector are embedded in the grooves, and the three-way channel communicates with the grooves; the connector is located below the elastic sheet, so that when the left and right ear tubes are forced away from each other and thus the lower surface of the elastic sheet presses against the top surface of the connector, the channel of the stethoscope-head tube communicates with the channels of the ear-hook tubes through the three-way channel of the connector and the grooves.

6. The combined structure of a rubber tube for a stethoscope and ear hooks according to claim 5, wherein a horizontal part of the T-shaped connector has a width no larger than that of the elastic sheet.

7. The combined structure of a rubber tube for a stethoscope and ear hooks according to claim 5, wherein at least two channels, which are intersected and communicate with each other, are provided in each of the ear-hook tubes, wherein an annular inner wall of the ear-hook tube constitutes the rubber tube channel, and a bottom side and side walls of the groove together define a groove channel.

8. The combined structure of a rubber tube for a stethoscope and ear hooks according to claim 5, wherein a first convex rib is provided on an inner bottom surface of a U-shaped portion of the rubber tube.

9. The combined structure of a rubber tube for a stethoscope and ear hooks according to claim 5, wherein second convex ribs are provided on an outer bottom surface of the U-shaped portion of the rubber tube at both sides of the U-shaped portion.

* * * * *